United States Patent
Raffle et al.

(12)

(10) Patent No.: US 9,201,512 B1
(45) Date of Patent: Dec. 1, 2015

(54) PROXIMITY SENSING FOR INPUT DETECTION

(75) Inventors: Hayes Solos Raffle, Palo Alto, CA (US); Yong Zhao, San Jose, CA (US)

(73) Assignee: Google Inc., Mountain View, CA (US)

(*) Notice: Subject to any disclaimer, the term of this patent is extended or adjusted under 35 U.S.C. 154(b) by 143 days.

(21) Appl. No.: 13/550,558

(22) Filed: Jul. 16, 2012

Related U.S. Application Data

(60) Provisional application No. 61/619,334, filed on Apr. 2, 2012.

(51) Int. Cl.
*G06F 3/033* (2013.01)

(52) U.S. Cl.
CPC .................................. *G06F 3/033* (2013.01)

(58) Field of Classification Search
CPC ..... G06F 3/0346; G06F 3/017; G06F 3/0304; G06F 3/038; G06F 3/04812; G06F 3/013; G06F 3/03547
USPC ........ 345/158; 351/209–223; 340/575, 573.1, 340/576; 341/20, 21
See application file for complete search history.

(56) References Cited

U.S. PATENT DOCUMENTS

| | | | |
|---|---|---|---|
| 4,081,623 A * | 3/1978 | Vogeley | 379/354 |
| 5,360,971 A | 11/1994 | Kaufman | |
| 5,570,151 A | 10/1996 | Terunuma | |
| 5,621,424 A | 4/1997 | Shimada | |
| 5,926,655 A | 7/1999 | Irie | |
| 6,163,281 A * | 12/2000 | Torch | 341/21 |
| 6,542,081 B2 | 4/2003 | Torch | |
| 6,920,283 B2 | 7/2005 | Goldstein | |
| 7,192,136 B2 | 3/2007 | Howell | |
| RE39,539 E | 4/2007 | Torch | |
| 7,255,437 B2 | 8/2007 | Howell | |
| 7,347,551 B2 * | 3/2008 | Fergason et al. | 351/210 |
| 7,380,936 B2 | 6/2008 | Howell | |
| 7,401,918 B2 | 7/2008 | Howell | |
| 7,401,920 B1 | 7/2008 | Kranz | |
| 7,438,410 B1 | 10/2008 | Howell | |
| 7,481,531 B2 | 1/2009 | Howell | |
| 7,500,746 B1 | 3/2009 | Howell | |
| 7,500,747 B2 | 3/2009 | Howell | |
| 7,515,054 B2 | 4/2009 | Torch | |

(Continued)

FOREIGN PATENT DOCUMENTS

| | | |
|---|---|---|
| JP | 2011221890 | 11/2011 |
| WO | 2011114092 | 9/2011 |

OTHER PUBLICATIONS

Arias, "Relation Between Intensity and Amplitude", Sep. 13, 2001.

(Continued)

*Primary Examiner* — Olga Merkoulova
(74) *Attorney, Agent, or Firm* — McDonnell Boehnen Hulbert & Berghoff LLP

(57) ABSTRACT

Disclosed is a technique that can help to detect a blink of an eye and a direction along which the eye is oriented before, after, or during the blink. To this end, light data can be received from at least one light sensor. The light data indicates at least one characteristic of light reflected from an eye area. A blink event can be detected based on the light data. A gaze direction can be determined based on the blink event. At least one computing action can be performed based on the gaze direction.

22 Claims, 6 Drawing Sheets

(56) References Cited

U.S. PATENT DOCUMENTS

| | | | |
|---|---|---|---|
| 7,543,934 B2 | 6/2009 | Howell | |
| 7,581,833 B2 | 9/2009 | Howell | |
| 7,621,634 B2 | 11/2009 | Howell | |
| 7,677,723 B2 | 3/2010 | Howell | |
| RE41,376 E | 6/2010 | Torch | |
| 7,760,898 B2 | 7/2010 | Howell | |
| 7,762,665 B2 | 7/2010 | Vertegaal | |
| 7,771,046 B2 | 8/2010 | Howell | |
| 7,792,552 B2 | 9/2010 | Thomas | |
| 7,806,525 B2 | 10/2010 | Howell | |
| 7,922,321 B2 | 4/2011 | Howell | |
| 8,073,198 B2 | 12/2011 | Marti | |
| 8,109,629 B2 | 2/2012 | Howell | |
| 8,160,311 B1 | 4/2012 | Schaefer | |
| 8,235,529 B1 | 8/2012 | Raffle | |
| 8,363,098 B2 | 1/2013 | Rosener | |
| 8,428,053 B2 | 4/2013 | Kannappan | |
| 8,723,790 B1 | 5/2014 | Schaefer | |
| 2001/0028309 A1* | 10/2001 | Torch | 340/575 |
| 2004/0183749 A1 | 9/2004 | Vertegaal | |
| 2005/0007552 A1* | 1/2005 | Fergason et al. | 351/210 |
| 2005/0119642 A1 | 6/2005 | Grecu et al. | |
| 2005/0264527 A1 | 12/2005 | Lin | |
| 2006/0103591 A1 | 5/2006 | Tanimura | |
| 2006/0115130 A1 | 6/2006 | Kozlay | |
| 2006/0192775 A1 | 8/2006 | Nicholson | |
| 2007/0024579 A1 | 2/2007 | Rosenberg | |
| 2007/0086764 A1 | 4/2007 | Konicek | |
| 2007/0201847 A1 | 8/2007 | Lei | |
| 2008/0211768 A1 | 9/2008 | Breen | |
| 2009/0115968 A1 | 5/2009 | Sugiyama | |
| 2009/0195497 A1 | 8/2009 | Fitzgerald | |
| 2010/0053555 A1 | 3/2010 | Enriquez et al. | |
| 2010/0066821 A1 | 3/2010 | Rosener | |
| 2010/0109895 A1 | 5/2010 | Rosener | |
| 2010/0110368 A1 | 5/2010 | Chaum | |
| 2010/0149073 A1* | 6/2010 | Chaum et al. | 345/8 |
| 2010/0235667 A1 | 9/2010 | Mucignat | |
| 2010/0295769 A1 | 11/2010 | Lundstrom | |
| 2011/0092925 A1 | 4/2011 | Voss | |
| 2011/0213664 A1 | 9/2011 | Osterhout | |
| 2011/0231757 A1 | 9/2011 | Haddick | |
| 2012/0019645 A1 | 1/2012 | Maltz | |
| 2012/0019662 A1 | 1/2012 | Maltz | |
| 2013/0135204 A1 | 5/2013 | Raffle | |
| 2013/0176533 A1 | 7/2013 | Raffle | |
| 2013/0257709 A1 | 10/2013 | Raffle | |
| 2013/0300652 A1 | 11/2013 | Raffle | |

OTHER PUBLICATIONS

Chau et al., "Real Time Eye Tracking and Blink Detection with USB Cameras", Boston University Technical Report No. 2005-12, May 12, 2005.

College of Engineering at the University of Wisconsin, "Device May Help Prevent 'Falling Asleep at the Switch'", Jan. 27, 1997.

Digi-Key Corporation, "Order page for Silicon Laboratories SI1140-A10-GMR", Mar. 15, 2012.

Eizenmann et al., "Precise Non-Contacting Measurement of Eye Movements Using the Corneal Reflex", Vision Research, vol. 24, Issue 2, pp. 167-174, 1984.

Silicon Labs, "Si1102 and Si1120 Designer Guides", Rev. 0.1, Oct. 2009, Silicon Laboratories.

Silicon Labs, "Si1143 Proximity/Ambient Light Sensor with I2C Interface", Nov. 19, 2010, Silicon Laboratories.

Tinker, "Apparatus for Recording Eye-Movements", The American Journal of Psychology, Jan. 1931, pp. 115-118, vol. 43, No. 1, University of Illinois Press.

International Search Report for corresponding international application No. PCT/US2013/034948 mailed Jul. 25, 2013.

Written Opinion for corresponding international application No. PCT/US2013/034948 mailed Jul. 25, 2013.

Pending U.S. Appl. No. 13/550,791, filed Jul. 17, 2012.

Pending U.S. Appl. No. 13/629,944, filed Sep. 28, 2012.

Emiliano Miluzzo et al., "EyePhone: Activating Mobile Phones With Your Eyes", MobiHeld 2010 Proceedings of the Second ACM SIGCOMM Workshop on Networking, Systems, and Applications on Mobile Handhelds, Aug. 30, 2010, pp. 15-20, published by Association for Computing Machinery, New York, NY, USA.

\* cited by examiner

PROXIMITY SENSING FOR INPUT DETECTION

CROSS-REFERENCE TO RELATED APPLICATIONS

This application claims the benefit of U.S. Provisional Application No. 61/619,334, filed on Apr. 2, 2012, the entirety of which is incorporated herein by reference.

BACKGROUND

Computing devices such as personal computers, laptop computers, tablet computers, cellular phones, and countless types of Internet-capable devices are increasingly prevalent in numerous aspects of modern life. Over time, the manner in which these devices are providing information to users is becoming more intelligent, more efficient, more intuitive, and/or less obtrusive.

The trend toward miniaturization of computing hardware peripherals, as well as of sensors, detectors, and image and audio processors, among other technologies, has helped open up a field sometimes referred to as "wearable computing." In the area of image and visual processing and production, in particular, it has become possible to consider wearable displays that place a very small image display element close enough to a wearer's eye(s) such that the displayed image fills or nearly fills the field of view, and appears as a normal sized image, such as might be displayed on a traditional image display device. The relevant technology may be referred to as "near-eye displays."

Near-eye displays are fundamental components of wearable displays, also sometimes called "head-mountable displays". A head-mountable display places a graphic display or displays close to one or both eyes of a wearer. To generate the images on a display, a computer processing system can be used. Such displays can occupy a wearer's entire field of view, or only occupy part of wearer's field of view. Further, head-mountable displays can be as small as a pair of glasses or as large as a helmet.

Emerging and anticipated uses of wearable displays include applications in which users interact in real time with an augmented or virtual reality. Such applications can be mission-critical or safety-critical, such as in a public safety or aviation setting. Nonetheless, often users must carry out complex and/or burdensome input procedures to perform desired computing functions. As a result, known methods for performing computing functions are often considered inconvenient, inefficient, and/or non-intuitive.

SUMMARY

This disclosure provides a method. The method includes receiving light data from at least one light sensor. The light data indicates at least one characteristic of light reflected from an eye area. The method also includes detecting a blink event based on the light data. The method also includes determining a gaze direction based on the blink event. The method also includes causing at least one computing action to be performed based on the gaze direction.

This disclosure also provides a system. The system includes at least one light sensor. The system also includes a computer-readable medium. The system also includes program instructions stored to the computer-readable medium. The program instructions are executable by at least one processor to perform functions, such as, for example, those discussed above in connection with the method.

This disclosure also provides a non-transitory computer-readable medium. The medium has stored thereon program instructions that, upon execution by at least one processor, cause a computing device to perform functions, such as, for example, those discussed above in connection with the method.

DETAILED DESCRIPTION

1. Overview

Disclosed herein are methods and systems that can help to detect a blink of an eye and a direction along which the eye is oriented before, after, or during the blink. This can be accomplished by detecting light reflected from an eye area. To this end, a blink-detection system can be used. The blink-detection system can include a light source that provides light to the eye area and a sensor that detects light reflected from the eye area. When the eye looks moves or blinks, the movement of the eyelids can cause changes in the intensity of light reflected from the eye area. The system can track the reflected light intensity. By doing so, the system can recognize the eye movements and determine the direction along which the eye is oriented before, after, or during the blink. The system can also determine various characteristics of the blinking motion.

In response to detecting a blink event, the system can perform a computing action, or can cause another system to perform a computing action. In some implementations, the system can perform the action in response to some blink events, while refraining from performing the action in response to other blink events. For example, a system can determine whether a blink is intentional or unintentional. (An unintentional blink can, for example, result from reflexes.) In this example, the system or another system performs an action in response to an intentional blink and does not perform the action in response to an unintentional blink. As another example, a system can perform an action in response to a blink event that occurs while the eye is oriented along a predetermined direction (e.g., "on screen"), while refraining from performing the action in response to blink events that occur while the eye is not oriented along the predetermined direction (e.g., "off screen").

2. Blink-Detection System Architecture a. Computing Systems

Figure 1A:
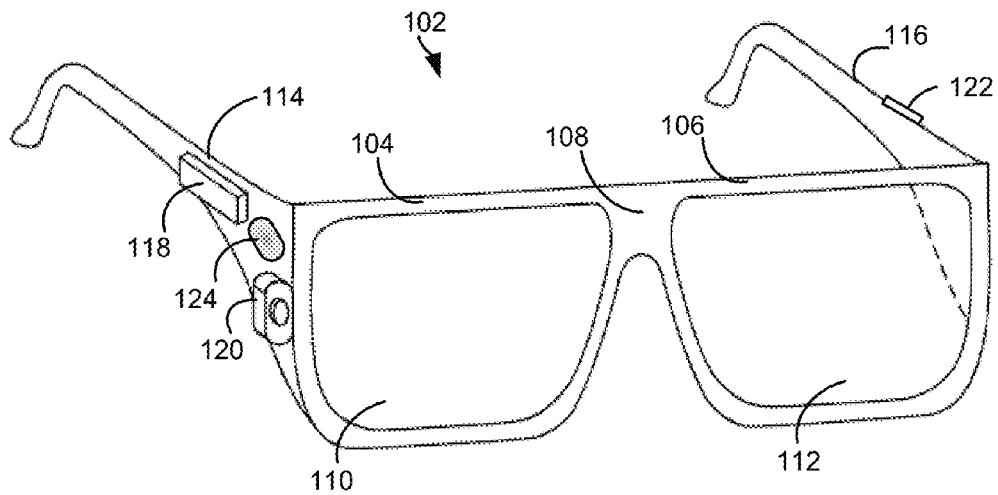
FIGS. 1A-1B illustrate an example of a wearable computing device.

FIG. 1A illustrates a wearable computing system 100, according to an embodiment. The wearable computing system 100 includes a blink-detection system 136. The wearable computing system 100 is shown in the form of a wearable computing device. While FIG. 1A illustrates a head-mountable device (HMD) 102 as an example of a wearable computing device, other types of wearable computing devices can be used. As illustrated in FIG. 1A, the HMD 102 includes frame elements, which include lens-frames 104, 106, a center frame support 108, lens elements 110, 112, and extending side-arms 114, 116. The center frame support 108 and the extending side-arms 114, 116 are configured to secure the HMD 102 to a user's face by way of a user's nose and ears.

Each of the frame elements 104, 106, 108 and the extending side-arms 114, 116 can be formed of a solid structure of plastic and/or metal, or can be formed of a hollow structure of similar material so as to allow wiring and component interconnects to be internally routed through the HMD 102. Other materials can be used as well.

One or more of each of the lens elements 110, 112 can be formed of any material that can suitably display a projected image or graphic. In addition, each of the lens elements 110, 112 can be sufficiently transparent to allow a user to see through the lens element. Combining these two features of the lens elements can facilitate an augmented reality or heads-up display by which the projected image or graphic is superimposed over a real-world view as perceived by the user through the lens elements.

The extending side-arms 114, 116 can each be projections that extend away from the lens-frames 104, 106, respectively, and can be positioned behind a user's ears to secure the HMD 102 to the user. The extending side-arms 114, 116 can further secure the HMD 102 to the user by extending around a rear portion of the user's head. In addition, the system 100 can connect to or be affixed within a head-mountable helmet structure. Other possibilities exist as well.

The system 100 can also include an on-board computing system 118, a video camera 120, a sensor 122, and a finger-operable touch pad 124. The on-board computing system 118 is shown to be positioned on the extending side-arm 114 of the HMD 102; however, the on-board computing system 118 can be provided on other parts of the HMD 102 or can be positioned remote from the HMD 102. For example, the on-board computing system 118 can be wire- or wirelessly-connected to the HMD 102. The on-board computing system 118 can include a processor and memory (not shown in FIG. 1A or 1B). The on-board computing system 118 can be configured to receive and analyze data from the video camera 120 and the finger-operable touch pad 124 (and, in some implementations, from other sensory devices, user interfaces, or both) and generate images for output by the lens elements 110 and 112. On-board computing system can take the form of computing system 300, discussed below in connection with FIG. 3.

Figure 1B:
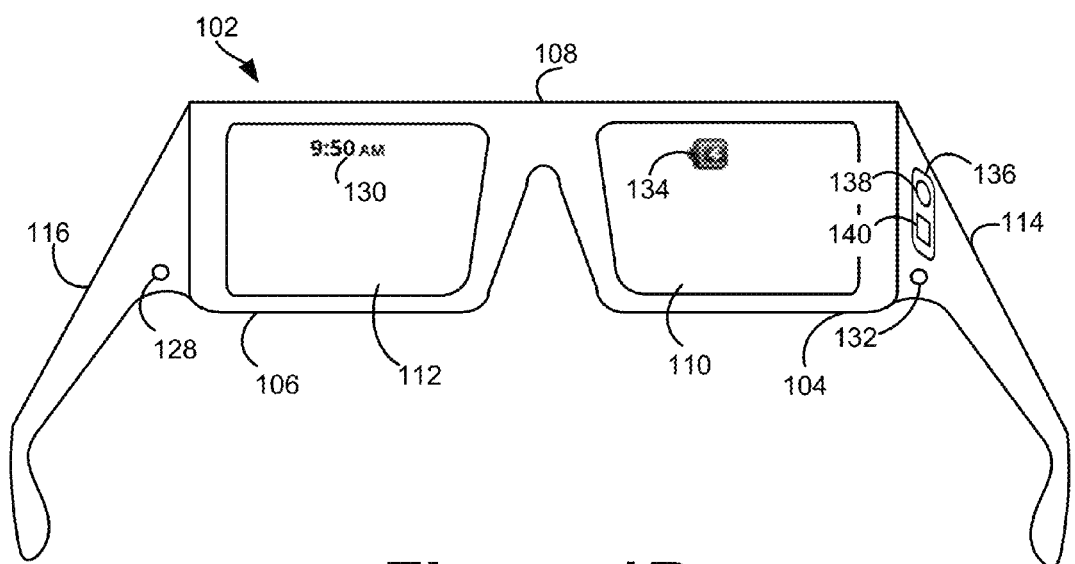

With continued reference to FIGS. 1A and 1B, the video camera 120 is shown positioned on the extending side-arm 114 of the HMD 102; however, the video camera 120 can be provided on other parts of the HMD 102. The video camera 120 can be configured to capture images at various resolutions or at different frame rates. Many video cameras with a small form-factor, such as those used in cell phones or webcams, for example, can be incorporated into an example of the system 100.

Although FIG. 1A illustrates one video camera 120, more video cameras can be used, and each video camera can be configured to capture the same view or to capture different views. For example, the video camera 120 can be forward facing to capture at least a portion of the real-world view perceived by the user. This forward facing image captured by the video camera 120 can then be used to generate an augmented reality in which computer generated images appear to interact with the real-world view perceived by the user.

The sensor 122 is shown on the extending side-arm 116 of the HMD 102; however, the sensor 122 can be positioned on other parts of the HMD 102. The sensor 122 can include various types of sensors, such as, for example, a gyroscope, an accelerometer, a proximity sensor, or any combination thereof. Other sensing devices can be included within, or in addition to, the sensor 122 or other sensing functions can be performed by the sensor 122.

The finger-operable touch pad 124 is shown on the extending side-arm 114 of the HMD 102. However, the finger-operable touch pad 124 can be positioned on other parts of the HMD 102. Also, more than one finger-operable touch pad can be present on the HMD 102. The finger-operable touch pad 124 can be used by a user to input commands. The finger-operable touch pad 124 can sense at least one of a position and a movement of a finger by way of capacitive sensing, resistance sensing, or a surface acoustic wave process, among other processes. The finger-operable touch pad 124 can be capable of sensing finger movement in a direction parallel or planar to the pad surface, in a direction normal to the pad surface, or both, and can be capable of sensing a level of pressure applied to the pad surface. The finger-operable touch pad 124 can be formed of one or more translucent or transparent insulating layers and one or more translucent or transparent conducting layers. Edges of the finger-operable touch pad 124 can be formed to have a raised, indented, or roughened surface, so as to provide tactile feedback to a user when the user's finger reaches the edge, or other area, of the finger-operable touch pad 124. If more than one finger-operable touch pad is present, each finger-operable touch pad can be operated independently, and can provide a different function.

FIG. 1B illustrates an alternate view of the system 100 illustrated in FIG. 1A. As shown in FIG. 1B, the lens elements 110, 112 can act as display elements. The HMD 102 can include a first projector 128 coupled to an inside surface of the extending side-arm 116 and configured to project a display 130 onto an inside surface of the lens element 112. A second projector 132 can be coupled to an inside surface of the extending side-arm 114 and can be configured to project a display 134 onto an inside surface of the lens element 110.

The lens elements 110, 112 can act as a combiner in a light projection system and can include a coating that reflects the light projected onto them from the projectors 128, 132. In some implementations, a reflective coating may not be used, such as, for example, when the projectors 128, 132 are scanning laser devices.

Other types of display elements can be used. For example, the lens elements 110, 112 themselves can include one or more of the following: a transparent or semi-transparent matrix display, such as, for example an electroluminescent display or a liquid crystal display; one or more waveguides for delivering an image to the user's eyes, or another optical element that is capable of delivering an in focus near-to-eye image to the user. A corresponding display driver can be disposed within the frame elements 104, 106 for driving such a matrix display. In addition, a laser or LED source and scanning system can be used to draw a raster display directly onto the retina of one or more of the user's eyes.

The blink-detection system 136 is shown in FIG. 1B as a light source 138 and a light sensor 140 that is affixed to the extending side-arm 114 of the HMD 102. As discussed below in connection with FIG. 2, a blink-detection system can include other more light sources or no light source at all, and can include elements other than those discussed in connection with the blink-detection system 136. In addition, the blink-detection system can be affixed to the HMD 102 in various other ways. For example, the light source 138 can be mounted separately from the light sensor 140. As another example, the blink-detection system 136 can be mounted to other frame elements of the HMD 102, such as, for example, the lens-frames 104 or 106, the center frame support 108, the extending side-arm 116, or combinations thereof.

Figure 1C:
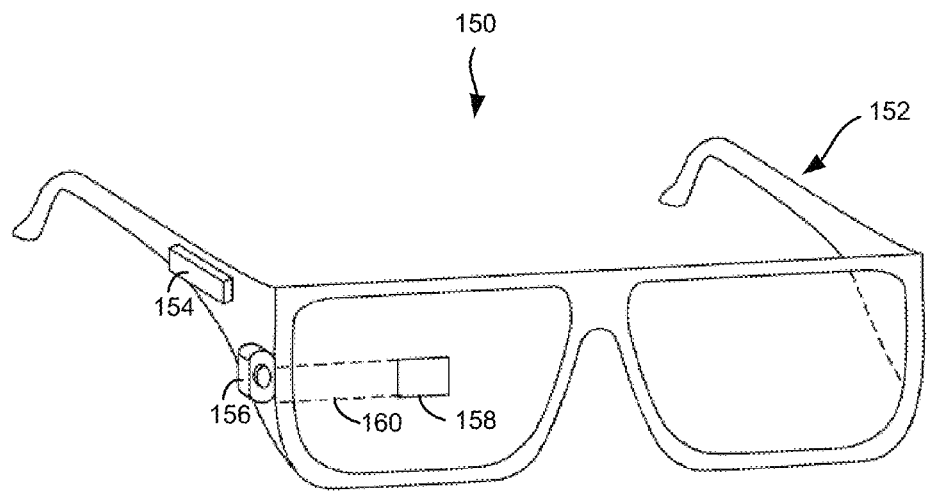
FIG. 1C illustrates another example of a wearable computing device.

FIG. 1C illustrates another wearable computing system 150, according to an embodiment. The wearable computing system is shown in the form of an HMD 152. The HMD 152 can be coupled to a blink-detection system (not shown in FIG. 1C). The HMD 152 can include frame elements and side-arms, such as those discussed above in connection with FIGS. 1A and 1B. In addition, the HMD 152 can include an on-board computing system 154 and a video camera 156, such as those discussed above in connection with FIGS. 1A and 1B. The video camera 156 is shown mounted on a frame of the HMD 152; however, the video camera 156 can be mounted at other positions as well.

As shown in FIG. 1C, the HMD 152 can include a single display 158, which can be coupled to the HMD. The display 158 can be formed on one of the lens elements of the HMD 152, such as a lens element discussed above in connection with FIGS. 1A and 1B, and can be configured to overlay computer-generated graphics in the user's view of the physical world. The display 158 is shown to be provided in a center of a lens of the HMD 152; however, the display 158 can be provided in other positions. The display 158 is controllable by way of the computing system 154, which is coupled to the display 158 by way of an optical waveguide 160.

Figure 1D:
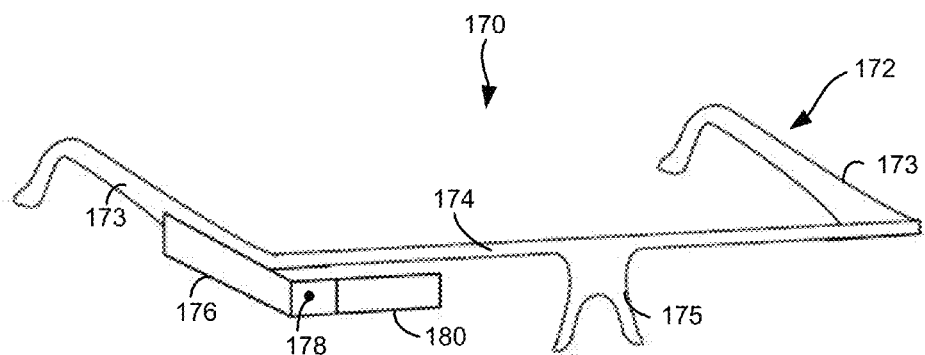
FIG. 1D illustrates another example of a wearable computing device.

FIG. 1D illustrates another wearable computing system 170. The wearable computing system 170 can include or connect to a blink-detection system (not shown in FIG. 1D). The wearable computing system 170 is shown in the form of an HMD 172. The HMD 172 can include side-arms 173, a center frame support 174, and a bridge portion with a nose-piece 175. The center frame support 174 connects the side-arms 173. The HMD 172 does not include lens-frames containing lens elements. In addition, the HMD 172 can include an on-board computing system 176 and a video camera 178, such as those discussed above in connection with FIGS. 1A and 1B.

The HMD 172 can include a single lens element 180, which can be coupled to one of the side-arms 173 or the center frame support 174. The lens element 180 can include a display, such as the display discussed above in connection with FIGS. 1A and 1B. The lens element 180 can be configured to overlay computer-generated graphics upon the user's view of the physical world. For example, the single lens element 180 can be coupled to the inner side of the extending side-arm 173—that is, the side exposed to a portion of a user's head when worn by the user. The single lens element 180 can be positioned in front of or proximate to a user's eye when the HMD 172 is worn by a user. For example, the single lens element 180 can be positioned below the center frame support 174, as shown in FIG. 1D.

b. Blink-Detection System

Figure 2:
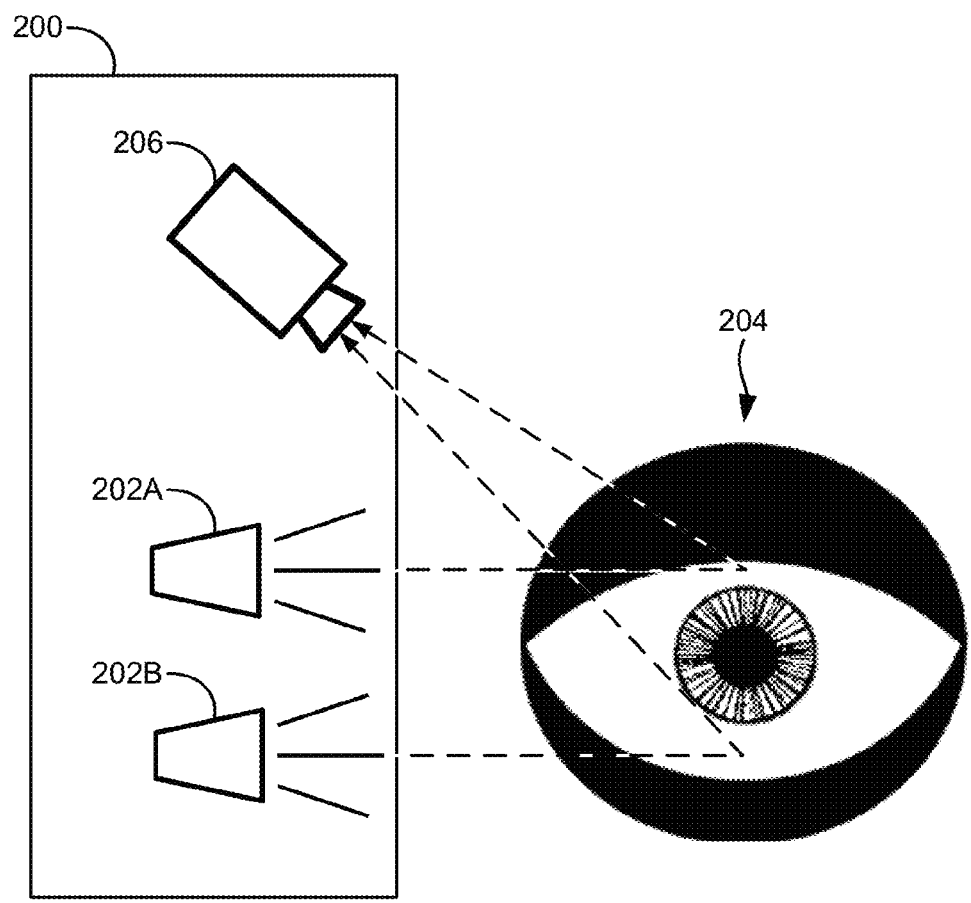
FIG. 2 illustrates an example of a blink-detection system.

FIG. 2 illustrates a blink-detection system 200, according to an embodiment. The blink-detection system 200 is shown to interact with an eye area 204. The eye area 204 can include the eye surface, eyelids, and portions of the user's face near the eye. The blink-detection system 200 includes two light sources 202A and 202B. The light sources 202A-202B are each configured to illuminate the eye area 204, as shown by the dashed lines. The blink-detection system 200 also includes a light sensor 206 that is configured to detect reflected light (also shown as dashed lines) from the eye area 204. The blink-detection system 200 can further include a processing unit (not shown in FIG. 2) that can perform computing functions. In particular, the processing unit can drive the light sources 202A-202B, receive readings from the light sensor 206, process the readings to determine aspects of the eye area 204, or perform combinations thereof. The processing unit can perform other functions as well.

i. Light Sources

In FIG. 2, the system 200 is shown to use two light sources 202A-202B to illuminate the eye area 204. While two light sources are shown, a blink-detection system can use any suitable number of light sources to illuminate the eye area. Further some systems may not include light sources at all. Instead, such systems can detect ambient light or other illumination coming from the eye area.

In systems using one or more light sources, each of the light sources can be any suitable type of light source. For example, the light source can include one or more light-emitting diodes (LEDs), laser diodes, incandescent sources, gas discharge sources, or a combination thereof. In addition, each of the light source can be integrated with the system or externally connected to the system, and can be driven by the light sensor or by a processing unit. Further, each of the light source can emit any frequency or intensity of light. In an embodiment, the light intensity can be in a range that is safe for use with the user's eye. In addition, light that is not visible to humans, such as, for example, infrared (IR) light, near-IR, or the like, can be used to avoid irritating the user. Depending on the desired implementation, however, some blink-detection systems can use visible light or high-intensity light for detection.

In some implementations, the light sources can be aimed at specific portions of the eye area. For example, as shown in FIG. 2, the light sources 202A-B are directed at the top and bottom of the eye, respectively. In some implementations, a single light source can be directed at the whole eye area or at one part of the eye area, such as, for example, one eyelid or the center of the eye. As another example, several light sources can each be aimed at respective various points on the eye area, mapping the eye at each of the various points.

Light sources can differ in the amount of the eye area that they illuminate. Such an area is termed a spot size. For example, one light source can have a spot size that provides light to the entire eye area. Another light source can focus on a relatively small point on the eye and, accordingly, have a relatively small spot size.

Further, the shape of the illuminated area can influence the behavior of the system. For example, if a light source illuminates a narrow horizontal area across the top of the eye area, the amount of reflected light can depend on whether the upper eyelid covers that particular height. As another example, a light source that provides light to the entire eye area can allow a system to detect the difference between a completely closed eye and an eye that is almost completely closed.

In addition, light sources can use modulated or pulsed light to distinguish each source from other sources and from ambient light. In particular, each light source can be configured to generate a pulse of light at a particular pattern so that the sensor can determine which light source generated the light based on the pulse pattern of the light. Since ambient light may not follow any such pattern, the light from the system's light sources can be distinguished from ambient-light noise by processing the measured light signal. Note that other light characteristics can be used to distinguish between light sources and ambient light. These light characteristics include, but are not limited to, frequency and intensity of the light.

In addition, the light sources can be configured to dynamically change characteristics of generated light, such as, for example, frequency, intensity, spot size/shape, focus, modulation or combinations thereof. Further, the light sources can couple with one or more mechanical actuators or servos to facilitate changing a given light source's position, light direction, or both. By way of actuators and/or devices for changing characteristics of the generated light, the system can allow for dynamic calibration and adjustments of the light sources.

ii. Light Sensor

In addition to the light sources 202A-202B, the blink-detection system 200 includes a light sensor 206 that is configured to detect light reflected from the eye area 204. As used in this disclosure, the term "reflected" can refer to a variety of interactions between light and an eye area, including those interactions that direct the light toward a light sensor. Examples of such interactions include mirror-reflection, diffuse reflection, and refraction, among other scattering processes. The light sensor 206 can be any type of light-sensitive element or device that is capable of outputting a measurable change in response to changes in light intensity. For instance, the light sensor 206 can be a photodiode, an electro-optical sensor, a fiber-optic sensor, a photo-detector, or a combination thereof, among others. In addition, the light sensor 206 can be configured to detect a specified frequency of light or a specified range of frequencies. In some implementations, the sensitivity of the light sensor 206 can be designed for specified frequencies and intensities of light.

The light sensor 206 can be positioned to detect light reflected from portions of the eye area. For example, the light sensor 206 can be positioned above the eye to detect light reflecting from the top of the eye when they eye is open, and from the upper eyelid when the eye is closed. In this way, the light sensor 206 can detect the amount of the eye that the upper eyelid covers. In some implementations, the light sensor 206 can be aligned at an oblique angle with respect to the eye area (similar to the alignment of the sensor 140 illustrated in FIG. 1B). In other arrangements, the light sensor 206 can point directly at the eye area and can be aimed at the center of the eye area.

In some implementations, a single sensor can be fitted with a single LED that is focused on an upper portion of an eye area; the upper portion can include, for example, an upper eyelid. The sensor can also incorporate a wide-angle sensor that is capable of determining the reflectivity of the eyelid. An eyelid generally tends to be more reflective when the user's eye is gazing downward or when the eye is closed than when the user's eye is gazing upward and when the eye is open. In addition, an eyelid generally tends to be even less reflective when the user's eye is gazing directly at the sensor.

In some implementations, a single LED can be used with multiple sensors. For example, one sensor can be aimed at an upper eyelid and another sensor can be aimed at a lower eyelid. For example, a single sensor can be fitted with two LEDs, with one being aimed at an upper eyelid and the other being aimed at a lower eyelid. As another example, a single sensor can be fitted with two LEDs, with one being aimed at a right portion of an eye area and the other being aimed at a left portion of the eye area. As yet another example, a single sensor can be fitted with multiple LEDs and can switch between the LEDs to distinguish readings from the LEDs.

In some arrangements, the system can detect light reflected from a second eye area. For example, the system can receive light data from another light sensor that can detect light from the second eye area. Alternatively, one light sensor can be positioned to detect light from both eye areas.

In some implementations, multiple sensors can be used to focus on both eyes of a user. For example, a sensor and illuminator can be focused on an outward corner of each eye. In this configuration, when the user blinks, both sensors generate a "spike," or impulse-like signal pattern at that moment.

Also, in this configuration, when the user winks, one of the sensors generates a spike, or impulse-like signal pattern at that moment. In this configuration, when the user looks up with his or her eyes open, both of the sensors generate a reduced signal level, whereas when the user looks down with his or her eyes open, both of the sensors generate an increased signal level. In addition, in this configuration, glances to the right or left can cause differential signals across two or more sensors, due in part to the user's eyes moving in unison.

Further, the system can be capable of adjusting and calibrating the behavior of the sensor, for example, by changing the position, direction, frequency response, sensitivity, detectable area size/shape of the sensor based on a context in which the system is used. For example, the sensor can be calibrated to a particular user, an intensity of ambient light, the light sources used, a battery-level of the device, or combinations thereof, among others. For example, the sensor can be coupled to mechanical actuators for changing its position and direction. As another example, the sensor can include changeable filters and baffles for filtering out different frequencies of light.

A sensor that detects light from multiple sources can differentiate between the signals from each source. For example, if the system uses a different pulsing pattern for each light source, then the sensor can separate signals based on the detected pulsing characteristics of detected light. In addition, the light sources can alternate when they illuminate the eye area. In such an arrangement, the sensor can associate a measurement of light with a source based on which source was on at the time that the light was measured. If the light sources illuminate different sections of the eye area, then the separate signals can be further associated with the respective eye-area portions. In other arrangements, the sensor can measure a single light intensity based on light from all the sources, without differentiating.

iii. Processing and Other Elements

The processing unit in the blink-detection system can be one of a general-purpose processor, a specialized processor, or a network of processors. The processor can be integrated with the light sensor or sources, or the processor can connect to the light sensor and sources by way of a bus or network connection. In addition, the processor can include or connect to a non-transitory computer-readable medium, such as a hard disk, a memory core, a memory drive, a server system, or combinations thereof, among other types of computer-readable mediums. The computer-readable medium can store at least the program instructions for directing the processor to execute functions associated with a blink-detection method.

The blink-detection system can include various other elements, such as, for example, additional processing, sensing, lighting, or interface elements. Some blink-detection systems can include a motion sensor, such as, for example, a gyroscope or an accelerometer, in order to detect when the system moves. This can help the system, for example, to determine whether a change in detected light could be due to a movement of the light sensor, with respect to the eye area, as opposed to a movement of the eyes or eyelids.

In some implementations, the blink-detection system can be integrated in or with a computing system, such as the wearable computing device discussed above in connection with FIGS. 1A-1D. Such systems can help a user to interface with the blink-detection system, for instance, to specify user-preferences, change system settings, perform calibration processes, or perform combinations thereof. Computing systems can also provide various other benefits for a blink-detection system, some of which are discussed in this section.

Figure 3:
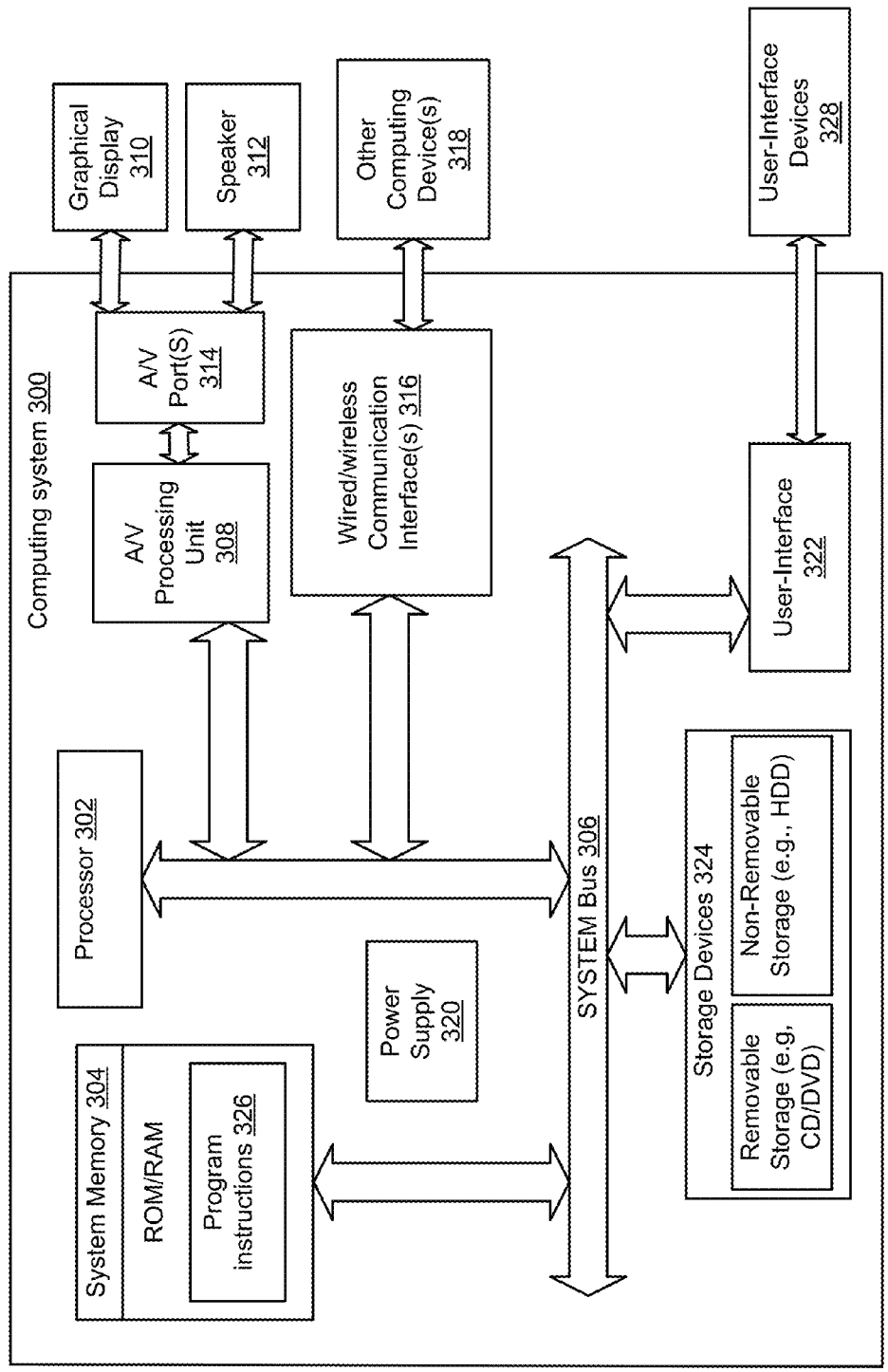
FIG. 3 illustrates an example of a computing system.

FIG. 3 illustrates an example of a computing system 300. The computing system 300 can include at least one processor 302 and system memory 304. In an embodiment, the computing system 300 can include a system bus 306 that communicatively connects the processor 302 and the system memory 304, as well as other components of the computing system 300. Depending on the desired configuration, the processor 302 can be any type of processor including, but not limited to, a microprocessor (µP), a microcontroller (µC), a digital signal processor (DSP), or any combination thereof. Furthermore, the system memory 304 can be of any type of memory now known or later developed including but not limited to volatile memory (such as RAM), non-volatile memory (such as ROM, flash memory, etc.), or any combination thereof.

The computing system 300 can include other components as well. For example, the computing system 300 is shown to include an A/V processing unit 308 for controlling a graphical display 310 and a speaker 312 (by way of an A/V port 314), one or more communication interfaces 316 for connecting to other computing devices 318, and a power supply 320. The graphical display 310 can be arranged to provide a visual depiction of various input regions provided by a user-interface 322. Note, also, that the user-interface 322 can be compatible with one or more additional user-interface devices 328 as well.

Furthermore, the computing system 300 can also include one or more data storage devices 324, which can be removable storage devices, non-removable storage devices, or a combination thereof. Examples of removable storage devices and non-removable storage devices include magnetic disk devices such as flexible disk drives and hard-disk drives (HDD), optical disk drives such as compact disk (CD) drives or digital versatile disk (DVD) drives, solid state drives (SSD), and/or any other storage device now known or later developed. Computer storage media can include volatile and nonvolatile, removable and non-removable media The computing system 300 can communicate using a communication link 316 (a wired or wireless connection) to a remote device 318. The remote device 318 can be any type of computing device or transmitter, including a laptop computer, a mobile telephone, tablet computing device, or combinations thereof. The remote device 318 can be configured to transmit data to the computing system 300. The remote device 318 and the computing system 300 can contain hardware to enable the communication link 316. Such hardware can include, for example, processors, transmitters, receivers, antennas, or combinations thereof, among other types of hardware.

In FIG. 3, the communication link 316 is illustrated as a wireless connection; however, wired connections can also be used. For example, the communication link 316 can be a wired serial bus such as a universal serial bus or a parallel bus, among other connections. The communication link 316 can also be a wireless connection using, for example, Bluetooth® radio technology, communication protocols described in IEEE 802.11 (including any IEEE 802.11 revisions), cellular technology (such as GSM, CDMA, UMTS, EV-DO, WiMAX, or LTE), Zigbee® technology, or combinations thereof, among other possibilities. Either of such a wired or wireless connection can be a proprietary connection as well. The remote device 330 can be accessible by way of the Internet and can include a computing cluster associated with a particular web service, such as, for example, social-networking, photo sharing, address book, or the like.

3. Operation

Figure 4:
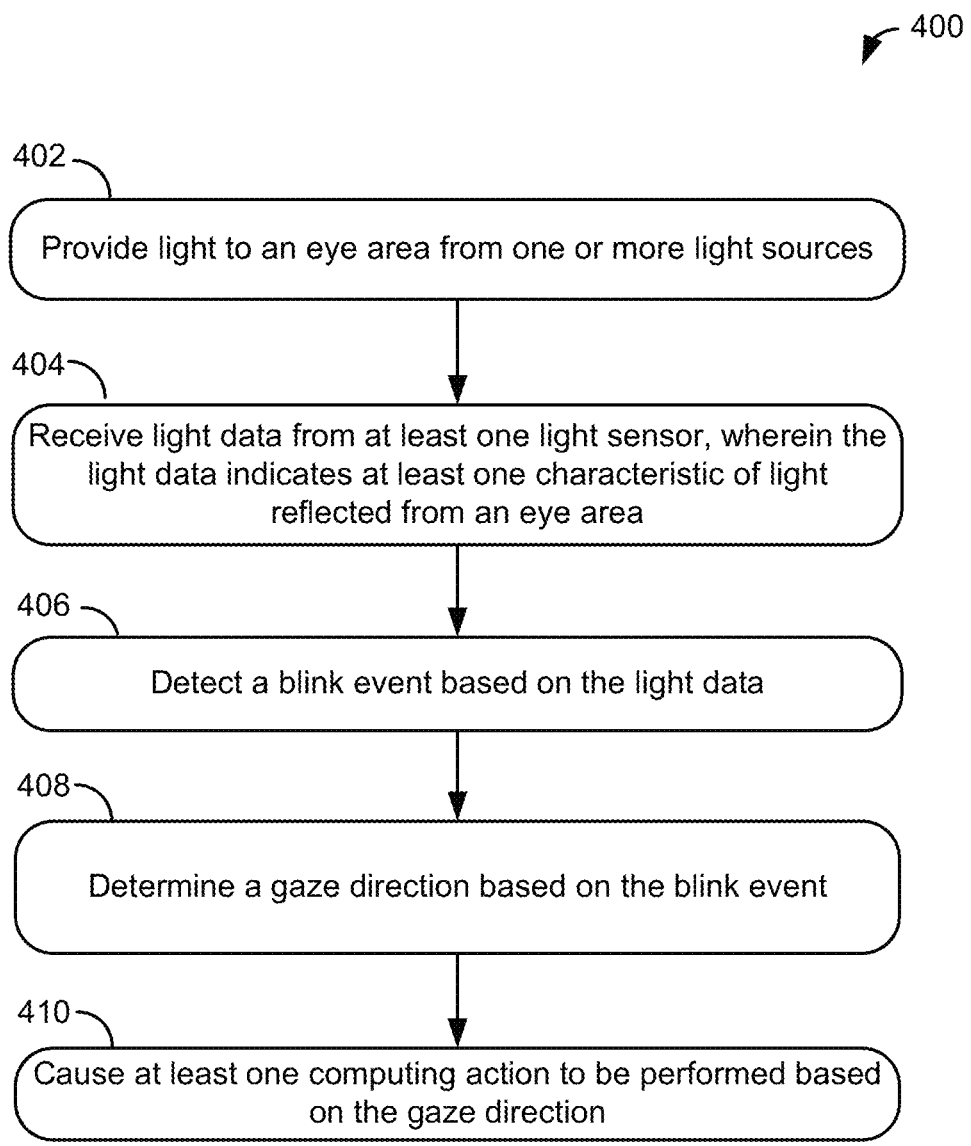
FIG. 4 is a flow chart illustrating a method, according to an embodiment.

FIG. 4 is a flow chart illustrating a method 400, according to an embodiment. The method 400 involves providing light to the eye area from one or more light sources, as shown by block 402. At block 404, the method 400 involves receiving light data from at least one light sensor. The light data indicates at least one characteristic of light reflected from the eye area. The method 400 further involves detecting a blink event based on the light data, at block 406. At block 408, the method 400 involves determining a gaze direction based on the blink event. And at block 410, the method 400 involves causing at least one computing action to be performed based on the gaze direction. Some embodiments may not involve step 402. Other exemplary embodiments can involve alternative and/or additional steps.

a. Providing Light to an Eye Area

As discussed above, a blink-detection system can include one or more light sources. These light sources can be controlled by a light sensor or by a processing unit. When in use, the light sources can provide light to portions of an eye area. The eye area can include the user's eye surface, eyelids, and the portions of the face around the eye. The light sources can provide light to some of the eye area or the entire eye area.

At block 402, the method 400 involves the system providing light to the eye area from one or more light sources. The light sources can constantly provide light to portions of the eye, or they can provide light to the eye intermittently. For example, the sources can alternate being on and off to facilitate distinguishing between the signals from each light source. Further, the on/off characteristics can help a sensor to differentiate between ambient light and artificial light signals. In some embodiments, a system can include both always-on and intermittent light sources.

Since each user can have a unique facial structure, some systems can calibrate the direction, position, and spot size/shape characteristics of the light sources based on detected facial characteristics. For example, a system can determine the direction from the light sources to the center of an eye area (using, for example, gaze tracking, glint detection, video recognition, or a combination thereof) and then change the arrangement of light sources to aim at the area around this center. Other arrangements are possible.

b. Receiving Light-Data from a Light Sensor

At block 404, the method 400 involves the system receiving light data from a light sensor. The light data indicates at least one characteristic of light reflected from the eye area. The sensor can be configured to detect certain aspects of the light such as frequency and intensity of the light. Other aspects can also be detected, such as polarization, coherence, phase, spectral width, modulation of the detected light, or combinations thereof, among others.

The light sensor can also be arranged to detect light reflected from a particular portion of the eye area or to detect light from the entire eye area. Additionally, the sensor can be specially designed to detect light with certain attributes, such as, for example, a certain frequency of modulation, a frequency of light, or light with a particular polarization.

Further, the system can calibrate and adjust the characteristics of the sensor. For example, if the sensor is used with near-IR light sources, the sensor can be configured to filter light that is not in the near-IR frequency range to avoid a noisy signal. As another example, if a blink-detection system is mounted high above the eye area, the system can detect the position of the eye and responsively aim the sensor lower to capture the eye area. As another example, in response to detecting that the light sources are not as bright as previously, the system can increase the sensitivity of the sensor to compensate for the lower light intensity.

The light data from the sensor can be received as discrete light-intensity measurements over time. Also, light data can represent one combined signal from all light sources and eye-area portions or the data can include multiple data sets with each data set representing a particular light source or detected portion of the eye area.

The intensity of light detected from a portion of the eye can change based on the characteristics of the eye at the specified point. In particular, a sensor can detect more light reflected from the skin surrounding the eye than light reflected off the surface (the sclera, cornea, or the like) of the eye, because of, among other considerations, the different light-scattering characteristics of human skin and eye surface. Therefore, an increase in detected light from a particular portion of the eye area can be indicative of an eye movement that increases the amount of skin that occupies the portion of the eye area from which the sensor is detecting light. For example, a sensor that detects light from the surface of an eye when the eye is open (relatively less light) can also detect light from the eyelid when the eye is closed (relatively more light).

Figure 5:
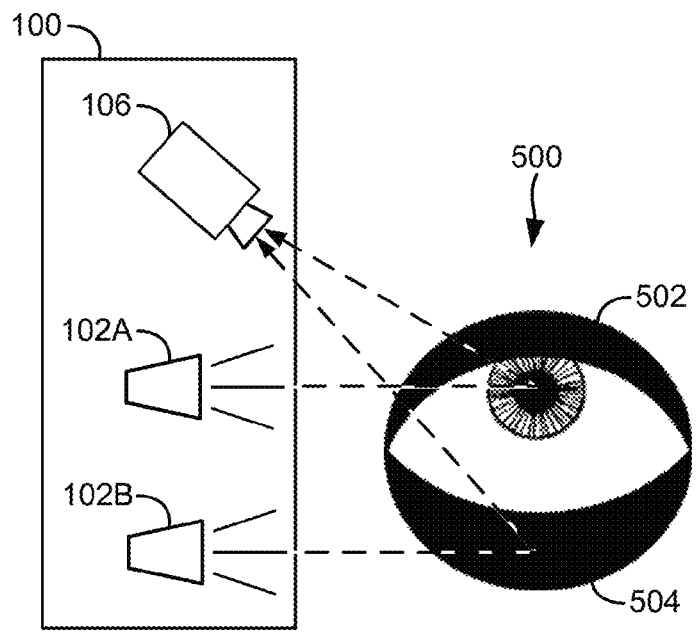
FIG. 5 illustrates the blink-detection system of FIG. 1 interacting with an eye area of an upward-looking user.

In addition to an eye closing, an increase in the light intensity detected by the sensor can also represent other eye movements. For example, FIG. 5 shows the detection system 100 from FIG. 1 interacting with the eye area 500 in which the eye is looking up. As shown, the bottom eyelid 504 has moved up into the path of the light from source 102B. Therefore, the intensity of the light detected by sensor 106 from the light source 102B can increase as a result of the eye movement, because more skin would be illuminated by this source than in the situation depicted in FIG. 1. Meanwhile, the light from the source 102A still illuminates the top of the eye, without illuminating the eyelid 502 as it does in the situation illustrated in FIG. 1. Hence, the intensity of light detected from the source 102B can remain unchanged, and the overall detected light intensity from both sources can therefore increase as a result of the eye movement.

Figure 6:
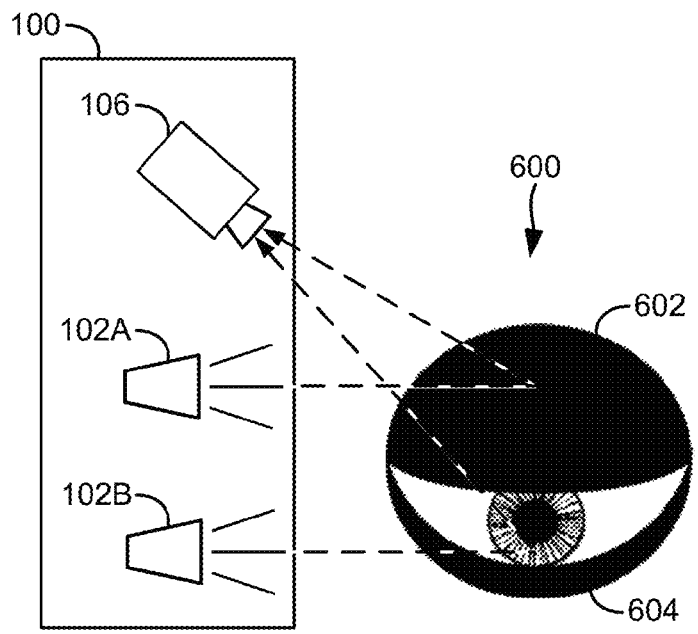
FIG. 6 illustrates the blink-detection system of FIG. 1 interacting with an eye area of a downward-looking user.

As another example, FIG. 6 shows the detection system 100 interacting with an eye area 600 in which the eye is looking down. As shown, the user's top eyelid 602 has moved down and into the path of the light from the source 102A. Therefore, the intensity of the light detected by the sensor 106 from the light source 102A can increase as a result of the eye movement, because more skin can be detected than in the situation depicted in FIG. 1. Meanwhile, the light from the source 102B still does not illuminate the top eyelid 602. Hence, the intensity of light detected from the source 102B would remain unchanged, and the overall detected light intensity from both sources can increase as a result of the eye movement.

c. Detecting a Blink Event

With reference to FIG. 4, the method 400, at block 406, involves detecting a blink event based on the light data. Due to the scattering characteristics of the skin and eye surface, when a blink event occurs (closing the eye entirely), the light detected by the blink-detection system can increase, as a result of an increase in the area of skin that is detected (or as a result of a decrease in the area of the eye that is detected). To detect when a blink event occurs, the system can therefore detect such changes in the light received by the light sensor.

Depending on the portions of the eye that are illuminated and measured, a blink can be detected in different ways. For example, in the system 100, the light from the top and bottom eyelids can be separately measured and increases in detected light can be recognized for each eyelid. In other arrangements, the movement of a single eyelid can be tracked, or the overall eye area can be measured.

In some implementations, the characteristics of a light increase can indicate whether the corresponding eye movement is a blink or some other movement. For example, the size of an increase can indicate whether the eyes are partially closed (as in a squint) or fully closed (as in a blink). As another example, the movement of closing both eyes (blink) can be faster than the movement of closing a single eye (wink). Further the system can use the duration of a blink, the eye-opening speed after the closure, changes in intensity while the eye is closed, or the like, as bases for determine that a particular signal indicates a blink event at the measured eye area.

The system can use techniques to determine whether the user is gazing at a particular area. For example, in an HMD with a small display, the entire display area can be considered an "area of interest." Accordingly, the HMD can determine if the user is gazing "on-screen." Such a gaze location can be determined using a calibrated threshold. In systems that detect lower and upper eyelid reflectivity, the sensors can show particular DC values when a user is gazing on-screen. Alternatively, the user can trigger an on-screen gaze by performing an eye gesture, such as, for example, gazing down and then quickly gazing up at the screen, followed by a fixed gaze. Signal processing techniques can compare user gestures to known classifiers of such gesture, signaling an event, such as a computing action, if the user performs the gesture.

On-screen and off-screen eye gestures can be determined through the placement of LEDs near various portions of the eye. For example, in an HMD having a small display mounted above the user's normal forward gaze, an LED can be focused on an upper eyelid, generally causing the reflectivity to decrease when the user looks up. Another LED can be focused on a lower eyelid, generally causing the reflectivity to decline when the user is gazing forward or downward. In addition, each of the LEDs can return blink gesture of larger deviation if the user is gazing at that LED during a given eye gesture.

d. Determining a Gaze Direction

In addition to detecting a blink event, the system can determine a gaze direction, representing the direction along which the eye is oriented during a blink, before the blink, or after the blink. In particular, the method 400, at block 408, involves determining the gaze direction based on the blink event. The system can determine the gaze direction based on characteristics of the detected light before, during, or after a blink event.

As shown in the illustrations of FIGS. 2, 5, and 6, the characteristics of the detected light can change based on the direction along which the eye is oriented before and after blinking. For example, the light detected by the system 100 can increase as a result of a user looking either up (as in FIG. 5) or down (as in FIG. 6). Hence, if the system 100 is configured to differentiate between the signals from the source 102A and the signals from the source 102B, the increases in light intensity from each source can be associated with corresponding eye movements.

To facilitate associating light-intensity data with eye-movement information, the system can collect and store representative light-intensity data for known eye movements. For example, the system can be programmed with characteristic light-intensity levels that correspond with a particular gaze direction. Alternatively, user-specific data can be gathered. For instance, a user can be instructed to follow a calibration procedure to store particular intensity data associated with the particular user's facial characteristics. In particular, the system can prompt the user to look in different directions. The prompting can be accomplished in various ways, such as for example, by audio or text commands, by displaying an indicator in the direction that the user should be looking, or by combinations thereof, among other possibilities. Then, the system can store the intensity of light that is detected from the user's eye area while the user is looking in the different directions.

Further, the system can adjust the representative light-intensity levels to better match the associated gaze directions. In particular, if the system determines that a representative level does not correctly represent the light that can be detected when the eye is looking in the associated gaze direction, then the system can responsively adjust the representative level to a level that does represent the light that can be detected when the eye is looking in the gaze direction. For example, if the system detects that the most common detected light-intensity level (likely associated with a user looking straight ahead) is much lower than the recorded intensity level associated with the straight ahead gaze direction, the system can responsively lower the representative level to match the previous readings.

Further, the system can calibrate the stored list of light-intensity levels for a context in which the method is used. For example, a system that is used by multiple users can store representative light-intensity levels for each user. When the user changes, the system can responsively change the list of levels that it uses.

The system can then compare light-intensity levels before and/or after the blink event to the characteristic or recorded readings. By matching the detected intensity level(s) to representative levels, the system can determine a possible gaze direction at the time of the blink.

Additionally, the system can store characteristic or user-specific light-intensity data related to gaze directions with eyes in a closed state. Then, the intensity level detected during a blink can be compared to the stored eye-closed intensity levels. In this way, the gaze direction can be determined by the light-data received during the blink in addition to the light-data received before and after the blink.

In other embodiments, the system can determine a gaze direction without referring to a list of representative data. For example, if the blink event occurs while the eye is looking forward, the difference between the light-intensity level before the blink event and the light-intensity level during the blink event can be much larger than if the user were looking either up or down. Therefore, the system can determine a first light-intensity level associated with an eye-open state and a second light-intensity level associated with an eye-closed state. Further, the system can determine that the difference in light-intensity is greater than a non-zero threshold difference and, based on this determination, determining that the gaze direction is an intermediate vertical direction; that is, between an upward and a downward direction. Similarly, the system can determining that the gaze direction is one of an upward and a downward direction, in response to determining that the difference in light-intensity is not greater than a non-zero threshold. Similar procedures can be used for comparing the intensity during a blink to the intensity after the blink.

e. Performing a Computing Action

At block 410, the method 400 involves causing at least one computing action to be performed based on the gaze direction. The blink-detection system can perform the computing action or send a command to cause a computing system to perform the computing action. In some cases, the system can perform different actions depending on certain characteristics of the blink event. For example, the system can refrain from performing a computing function in response to detecting a blink with certain characteristics, and perform the action in response to detecting a blink with other characteristics. In particular, the system can determine at least one computing action to be performed, based at least on the gaze direction and then perform the determined action.

As a particular example, a system can determine, based on received light data, that a blinking motion is not an intentional input-blink, but rather that the blink is a reflexive blink (a natural blink due to a user's reflexes). In particular, a reflexive blink can be very short in comparison to a non-reflexive blink (which can be an intentional blink). Hence, if a blink lasts longer than a threshold time, then the blink can be considered an intentional blink, whereas if the blink does not last longer than the threshold time, then the blink can be considered an unintentional blink. In such an implementation, the system can perform a specified action, or refrain from performing the specified action, in response to determining that a blink is an unintentional blink. Of course, the system can instead perform the specified action, or refrain from performing the specified action, in response to determining that the blink is an intentional blink.

As a further example, a system can perform the specified action in response to blinks in which the eye is facing a certain direction. In particular, the system can make a determination that the gaze direction is one of a predetermined set of directions and responsively determine the action to be performed based on the determination. For example, the system can store a range of directions that are "on screen" and a range of directions that are "off screen". When the user is looking relatively forward—that is, towards an intermediate vertical direction, as shown in FIG. 1, when blinking—the system can recognize the blink event as on-screen blink and responsively determine a computing action to be performed. In contrast, when the user is looking upward or downward while blinking, the system can recognize the blink event as off-screen blinking and responsively refrain from performing the computing action.

In some implementations, the system can perform different actions in response to blinks in which the user is looking at different directions. For example, the system can perform one action in response to on-screen blinking and another action in response to off-screen blinking. As another example, the system can set several direction ranges associated with various different actions and then perform the actions in response to the user looking in each respective direction range. For this reason, the system can first determine an action to perform in response to a detected blink and then perform the determined action. A system can also condition performance of a specified action on other characteristics of a blinking motion or other contexts.

The computing action can be any function that can be executed by the blink-detection system, an attached computing system, or a combination thereof. As an example, the specified action could be a select function (similar to the select function that a computer executes in response to detecting a mouse-click). As another example, a system can perform a function associated with an application running on the device in response to detecting blinking. In some implementations, multiple computing actions can be performed in response to detecting a blink. Various other functions can be performed in response to detecting a blink.

4. Conclusion

While this disclosure discusses various aspects and embodiments, other aspects and embodiments will be apparent to those skilled in the art. The various aspects and embodiments discussed in this disclosure are for purposes of illustration and are not intended to be limiting, with the true scope and spirit being indicated by the following claims.

We claim:

1. A method comprising:
   receiving light data from at least one light sensor, wherein the light data indicates at least one characteristic of light reflected from an eye area;
   detecting a blink event based on the light data, wherein detecting the blink event comprises detecting, in a given portion of the light data, a first light-intensity level and a subsequent second light-intensity level, wherein the first light-intensity level is associated with an eye-open state, and wherein the second light-intensity level is associated with an eye-closed state;
   determining a particular gaze direction based on the given portion of the light data, wherein determining the particular gaze direction comprises: (i) determining a difference between the first and second light-intensity levels, and (ii) determining that the difference between the first and second light-intensity levels corresponds to the particular gaze direction; and
   causing at least one computing action to be performed based on the particular gaze direction.

2. The method of claim 1, further comprising providing light to the eye area by way of one or more light sources.

3. The method of claim 1,
   wherein determining that the difference between the first and second light-intensity levels corresponds to the particular gaze direction comprises (i) determining whether the difference between the first and second light-intensity levels exceeds a threshold, and (ii) determining that the particular gaze direction is an intermediate vertical direction in response to a determination that the difference between the first and second light-intensity levels exceeds the threshold.

4. The method of claim 1, direction based on the blink event comprises:
   wherein determining that the difference between the first and second light-intensity levels corresponds to the particular gaze direction comprises (i) determining whether the difference between the first and second light-intensity levels exceeds a threshold, and (ii) determining that the particular gaze direction is either an upward direction or a downward direction in response to a determination that the difference between the first and second light-intensity levels is less than the threshold.

5. The method of claim 1, further comprising:
   storing a plurality of light-intensity levels each corresponding to the eye-open state, wherein each of the plurality of light-intensity levels is associated with a corresponding gaze direction; and
   calibrating each of the plurality of light-intensity levels for a context in which the method is used.

6. The method of claim 1, wherein causing the at least one computing action to be performed based on the particular gaze direction comprises determining the at least one computing action based on the particular gaze direction.

7. The method of claim 6, wherein determining the at least one computing action based on the particular gaze direction comprises:
   determining whether the particular gaze direction corresponds to at least one of a predetermined set of directions; and
   determining the at least one computing action in response to a determination that the particular gaze direction corresponds to the at least one of the predetermined set of directions.

8. The method of claim 1, wherein determining the at least one computing action further comprises:
   determining whether the blink event is an intentional input blinking based on the light data; and
   determining the at least one computing action in response to a determination that the blink event is the intentional input blinking.

9. A system comprising:
   at least one light sensor;
   a computer-readable medium;
   program instructions stored to the computer-readable medium and executable by at least one processor to perform functions comprising:
   (i) receiving light data from the at least one light sensor, wherein the light data indicates at least one characteristic of light reflected from an eye area;
   (ii) detecting a blink event based on the light data, wherein detecting the blink event comprises detecting, in a given portion of the light data, a first light-intensity level and a subsequent second light-intensity level, wherein the first light-intensity level is associated with an eye-open state, and wherein the second light-intensity level is associated with an eye-closed state;
   (iii) determining a particular gaze direction based on the given portion of the light data, wherein determining the particular gaze direction comprises: (a) determining a difference between the first and second light-intensity levels, and (b) determining that the difference between the first and second light-intensity levels corresponds to the particular gaze direction; and
   (iv) causing at least one computing action to be performed based on the particular gaze direction.

10. The system of claim 9, further comprising a light source, wherein the light source is operable to provide light to the eye area.

11. The system of claim 10, wherein the light source is operable to provide light to at least one of an upper-eyelid area of the eye area or a lower-eyelid area of the eye area, and wherein the light data indicates characteristics of at least one of light reflected from the upper-eyelid area and light reflected from the lower-eyelid area.

12. The system of claim 9, wherein the at least one light sensor is aligned at an oblique angle with respect to the eye area.

13. The system of claim 9, further comprising a head-mountable device, wherein the computer-readable medium is integrated in the head-mountable device, and wherein the at least one light sensor is affixed to the head-mountable device.

14. The system of claim 9, further comprising a motion sensor, wherein the program instructions are further executable by the at least one processor to perform functions comprising receiving motion data by way of the motion sensor, and wherein detecting the blink event is further based on the motion data.

15. The system of claim 9,
    wherein determining that the difference between the first and second light-intensity levels corresponds to the particular gaze direction comprises (i) determining whether the difference between the first and second light-intensity levels exceeds a threshold, and (ii) determining that the particular gaze direction is an intermediate vertical direction in response to a determination that the difference between the first and second light-intensity levels exceeds the threshold.

16. The system of claim 9,
    wherein determining that the difference between the first and second light-intensity levels corresponds to the particular gaze direction comprises (i) determining whether the difference between the first and second light-intensity levels exceeds a threshold, and (ii) determining that the particular gaze direction is either an upward direction or a downward direction in response to a determination that the difference between the first and second light-intensity levels is less than the threshold.

17. The system of claim 9, wherein causing the at least one computing action to be performed based on the particular gaze direction comprises determining the at least one computing action based on the particular gaze direction.

18. The system of claim 17, wherein the program instructions are further executable by the at least one processor to perform functions comprising:
- determine whether the particular gaze direction corresponds to at least one of a predetermined set of directions; and
- determine the at least one computing action in response to a determination that the particular gaze direction corresponds to the at least one of the predetermined set of directions.

19. A non-transitory computer-readable medium having stored thereon program instructions that, upon execution by at least one processor, cause a computing device to perform functions comprising:
- receiving light data from at least one light sensor, wherein the light data indicates at least one characteristic of light reflected from an eye area;
- detecting a blink event based on the light data, wherein detecting the blink event comprises detecting, in a given portion of the light data, a first light-intensity level and a subsequent second light-intensity level, wherein the first light-intensity level is associated with an eye-open state, and wherein the second light-intensity level is associated with an eye-closed state;
- determining a particular gaze direction based on the given portion of the light data, wherein determining the gaze direction comprises: (i) determining a difference between the first and second light-intensity levels, and (ii) determining that the difference between the first and second light-intensity levels corresponds to the particular gaze direction; and
- causing at least one computing action to be performed based on the particular gaze direction.

20. The non-transitory computer-readable medium of claim 19, wherein the functions further comprise providing light to the eye area by way of one or more light sources.

21. The non-transitory computer-readable medium of claim 19, wherein causing the at least one computing action to be performed based on the particular gaze direction comprises:
- determining whether the particular gaze direction corresponds to at least one of a predetermined set of directions; and
- determining the at least one computing action in response to a determination that the particular gaze direction corresponds to the at least one of the predetermined set of directions.

22. The non-transitory computer-readable medium of claim 19, wherein the functions further comprise:
- determining the particular gaze direction by (i) comparing the first light-intensity level to a plurality of predetermined light-intensity levels, wherein each predetermined light-intensity level corresponds to a given gaze direction, and (ii) based on the comparison, determining that the first light-intensity level corresponds to the particular gaze direction.

* * * * *